US00PP28075P2

(12) United States Plant Patent
Lane

(10) Patent No.: US PP28,075 P2
(45) Date of Patent: Jun. 6, 2017

(54) ***MALUS* TREE NAMED 'SPA493'**

(50) Latin Name: *Malus domestica*
Varietal Denomination: SPA493

(71) Applicant: William David Lane, Summerland (CA)

(72) Inventor: William David Lane, Summerland (CA)

(73) Assignee: HER MAJESTY THE QUEEN IN RIGHT OF CANADA AS REPRESENTED BY THE MINISTER OF AGRICULTURE AND AGRI-FOOD, Ottawa, Ontario (CA)

( * ) Notice: Subject to any disclaimer, the term of this patent is extended or adjusted under 35 U.S.C. 154(b) by 49 days.

(21) Appl. No.: 14/545,549

(22) Filed: May 20, 2015

Related U.S. Application Data

(60) Provisional application No. 61/997,017, filed on May 20, 2014.

(51) Int. Cl.
*A01H 5/08* (2006.01)

(52) U.S. Cl.
USPC ..... Plt./161

(58) Field of Classification Search
USPC ..... Plt./161
See application file for complete search history.

(56) References Cited

PUBLICATIONS

Bourque. 2009. Botany Photo of the Day.*
Hampson et al. Can J. Plant Sci. 93: 979-982, 2013.*

* cited by examiner

*Primary Examiner* — Keith Robinson
(74) *Attorney, Agent, or Firm* — Penny J. Aguirre

(57) ABSTRACT

A new cultivar of apple tree, 'SPA493', that is characterized by its spreading tree habit that is easy to manage, its moderate growth rate, its medium sized fruit that is globose in shape, its fruit with a sweet-tart flavor, its fruit with skin that is yellow in color heavily blushed with red, its fruit that has a very long storage period, and its mid to late harvest period in British Columbia, Canada.

2 Drawing Sheets

Botanical classification: *Malus domestica.*
Varietal denomination: 'SPA493'.

BACKGROUND OF THE INVENTION

The present invention relates to a new and distinct cultivar of apple tree, botanically known as *Malus domestica* 'SPA493', referred to hereafter by its cultivar name, 'SPA493'.

The new cultivar arose from a cross made by the Inventor in Summerland, British Columbia, Canada 1981 between 'Splendour' (U.S. Plant Pat. No. 2,460) as the female parent and 'Gala' (U.S. Plant Pat. No. 3,637) as the male parent. The Inventor selected 'SPA493' as a single unique plant amongst the seedlings that resulted from the above cross in 1997.

Asexual propagation of the new cultivar was first accomplished by vegetative budding onto 'M26' apple tree rootstock in 1997 under the direction of the Inventor in Summerland, BC, Canada. Asexual propagation by vegetative budding and grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SPA493' as a unique cultivar of apple tree.

1. 'SPA493' exhibits a spreading tree habit that is easy to manage.
2. 'SPA493' exhibits medium sized fruit that is globose in shape.
3. 'SPA493' exhibits fruit with a sweet-tart flavor.
4. 'SPA493' exhibits fruit with skin that is yellow in color heavily blushed with red.
5. 'SPA493' exhibits fruit that has a very long storage period.
6. 'SPA493' exhibits a moderate growth rate.
7. 'SPA493' exhibits a mid to late harvest period in British Columbia, Canada.

The female parent of 'SPA493', 'Splendour', differs from 'SPA493' in having fruit that is larger in size, ovoid-conical in shape, and green-yellow color, and in having an earlier harvest date. The male parent of 'SPA493', 'Gala', is similar to 'SPA493' in having fruit that is bicolored and medium in size, and in having a moderate growth rate. 'Gala', differs from 'SPA493' in having fruit that is conical in shape, in having fruit with moderate storability, and in having a more difficult to manage plant habit. 'SPA493' can also be compared to the apple tree cultivars 'Ambrosia' (U.S. Plant Pat. No. 10,789), 'Royal Gala' (U.S. Plant Pat. No. 4,121), and 'BC2' (unpatented). All three reference varieties differ from 'SPA493' in having fruit that is larger in size, in having leaves that are smaller in size, in having a later flowering habit, and in having shorter and thicker peduncles. 'Ambrosia' differs from 'SPA493' in having fruit that is globose-conical in shape and creamy-white in color, in having fruit with moderate storability and a very sweet flavor, and in having an earlier harvest date. 'Royal Gala' differs from 'SPA493' in having fruit that is globose-conical in shape and streaked and flecked red in color, and in having an earlier harvest date. 'BC2' differs from 'SPA493' in having fruit that is ellipsoid-conical in shape and green-yellow in color blushed red to dark red, and in having a later harvest date.

BRIEF DESCRIPTION OF THE DRAWINGS

The accompanying colored photograph illustrates the overall appearance and distinct characteristics of the new apple tree. The photograph was taken of fruit of a 7 year-old plant of 'SPA493' as grown outdoors in the ground on 'M26' apple rootstalk in Summerland, BC, Canada.

The photograph in FIG. 1 provides a close-up view of a line of trees of 'SPA493'.

Figure 1:
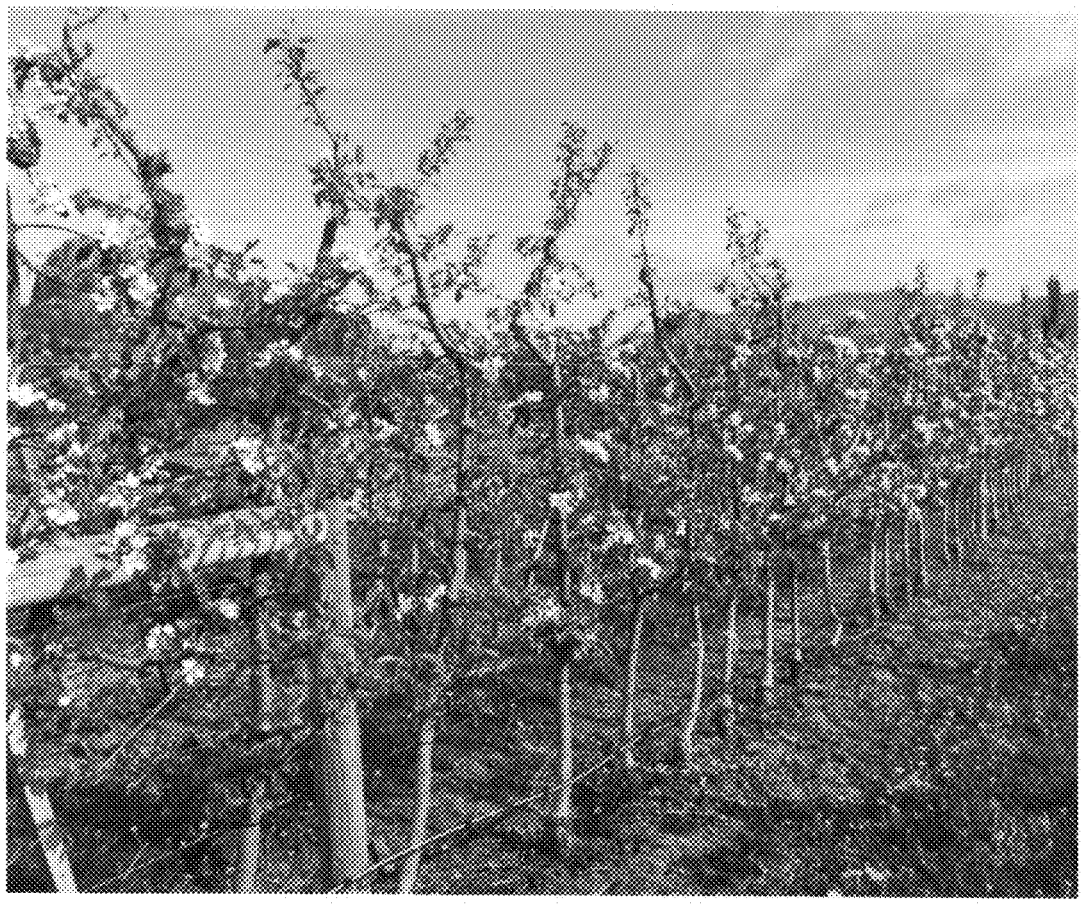
Figure 2:
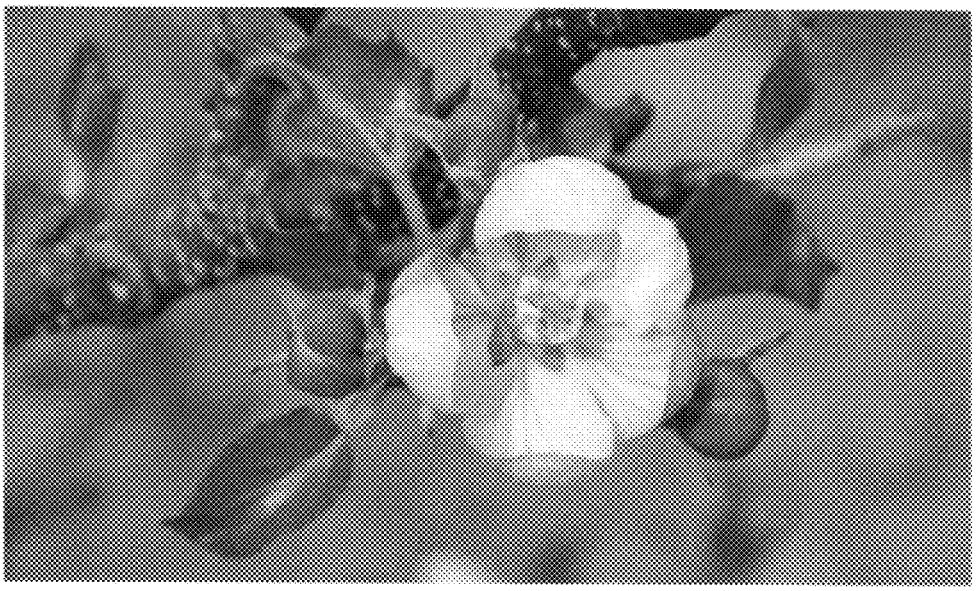

The photograph in FIG. 2 provides a close-up view of a flower and flower buds of 'SPA493'.

Figure 3:
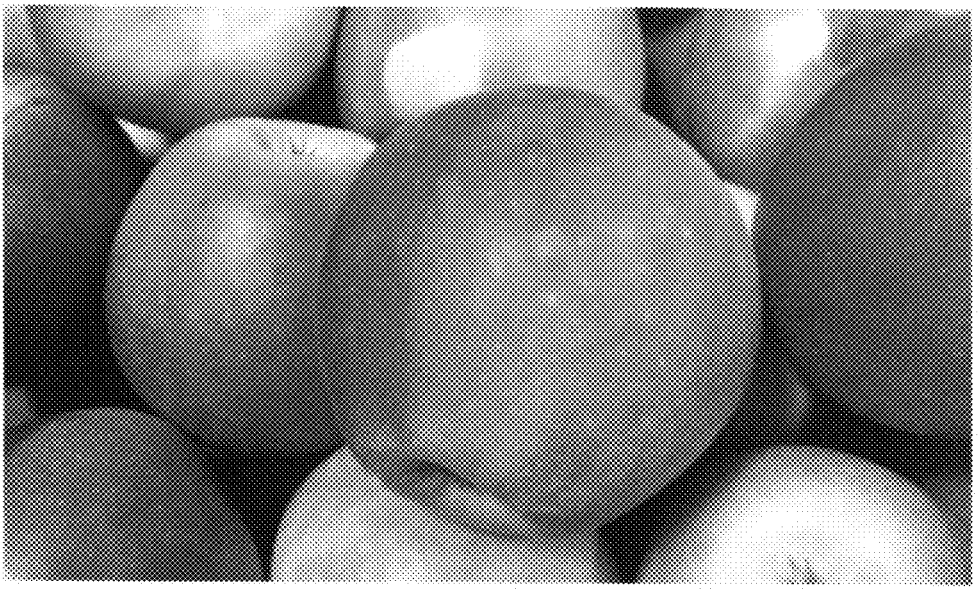

The photograph in FIG. 3 provides a close-up view of the fruit of 'SPA493'.

The colors in the photograph are as close as possible with the photographic and printing technology utilized and the color values cited in the detailed botanical description accurately describe the colors of the new apple tree.

DETAILED BOTANICAL DESCRIPTION

The following is a detailed description of the new apple variety as observed on 7 year-old plants as grown outdoors in the ground on 'M26' apple rootstalk in Summerland, BC, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Tree description:

*Plant type*.—Deciduous fruiting tree.

*Plant habit*.—Spreading.

*Height and spread*.—An average of 3.57 m in height and 26.8 cm in width.

*Cold hardiness*.—At least to U.S.D.A. Zone 4.

*Diseases and pests*.—No susceptibility or resistance to diseases or pests has been observed.

*Propagation*.—Vegetative budding and grafting.

*Growth rate*.—Moderate.

Description of branches:

*Frequency*.—Medium.

*Angle*.—Approximately 90° angle to trunk.

*Bearing*.—Predominance of bearing on spurs.

*Bark color*.—187A and 183A.

Description of one year-old shoots:

*Pubescence on upper one year-old shoot*.—Weak to medium on upper side.

*Shine of bark*.—Moderate.

*Flexibility*.—Medium to strong.

*Thickness of shoot at center of middle internode*.—Average of 5.13 mm.

*Bark color* (*using bark on* 1 *year old shoots exposed to sun*).—178A.

*Shoot angle*.—Approximately 90°.

*Lenticel*.—Circular in shape, <1 mm in diameter, 11 per square cm of shoot, color 164D to 165B on sun exposed side.

*Internode length*.—Average of 3.4 cm.

Description of growing shoots:

*Color of growing tip of shoot*.—193B.

*Shape of shoot tips leaves in cross section*.—Concave.

*Pubescence of shoot tip leaves*.—Weak on upper surface.

*Color of shoot tip leaves*.—147D on lower surface and 144A on upper surface.

*Distribution of color other than green on shoot tips leaves*.—None.

Leaf description:

*Leaf orientation*.—Upward.

*Leaf division*.—Simple.

*Leaf shape*.—Ovate.

*Leaf size*.—Average of 10.3 cm in length and 6.2 cm in width.

*Leaf apex*.—Cuspidate.

*Leaf base*.—Oblique or obtuse.

*Leaf surface*.—Upper surface; slightly glossy, lower surface; moderately pubescent.

*Leaf margin*.—Serrate.

*Leaf color*.—Upper surface 146C, lower surface 146A.

*Leaf anthocyanin on lower surface*.—None.

*Leaf venation*.—Pinnate main veins with netted minor veins.

*Petiole size*.—Average of 3.81 cm in length and 1.51 mm in diameter.

*Petiole color*.—145C with a tinge of anthocyanin at base 186A.

*Stipules*.—Small to medium in size (mean 0.6 cm in length), found on actively growing shoots where they are present on newly developed leaves but sometimes abscising on older leaves.

Flower description:

*Blooming period*.—Mid-season; early to mid-May in British Columbia, Canada.

*Number of flowers*.—Average of 5 per spur.

*Inflorescence type*.—Corymb of rotate flowers.

*Flower buds*.—At pink tip stage; 67B in color, round to conical in shape.

*Flower size*.—Average of 5.2 cm in diameter and 0.4 cm in depth.

*Flower fragrance*.—Mild.

*Flower aspect*.—Upright.

*Petals*.—5 per flower, unfused, sometimes overlapping, ovate in shape, obtuse apex, round base, entire margin, about 2.3 cm in length and 1.5 cm in width, color of upper surface when opening and mature; 155D with tinges of 64D, color of lower surface when opening and mature; 155D with tinges of 64D, upper and lower surface glabrous, slight to moderately pubescent on both surfaces.

*Sepals*.—5, color upper surface 138C, slight to moderately pubescent on both surfaces, triangular in shape, entire margin, acute apex, touching to overlapping at base, average of 6.7 mm in length (medium) and 2.9 mm in width.

*Pedicel*.—138B in color on side exposed to sun, average of 3.4 cm in length and 2 mm in width, glabrous surface.

*Peduncle*.—An average of 2.7 cm in length and 2.9 mm in width, 173A in color, surface is course and fibrous.

*Pistil.*—19, compound carpel with 5 stigmas (circular in shape) fused at base, 7.7 mm in length, style is 145C in color and 8 mm in length, stigma is 175D in color, ovary is pubescent and 137B in color.

*Stamens.*—Average of 15, average of 1.1 cm in length, anther is oblong in shape, 155D in color and 2 mm in length, filament is 155D in color and an average of 9 mm in length, pollen is 164B in color and moderate in quantity.

Fruit description:

*Fruit size.*—Medium, 8.0 cm in diameter, average of 6.7 cm in height.

*Position of maximum diameter.*—Midway between proximal and distal ends.

*Fruit shape.*—Globose.

*Fruit symmetry.*—Symmetrical.

*Fruit prominence of ribbing.*—Not present.

*Fruit aperture of eye.*—Open, an average of 6.4 mm in diameter.

*Persistence of calyx.*—Persistent.

*Length of sepal.*—Average of 8 mm.

*Spacing of sepals at base.*—Touching to overlapping

*Eye basin.*—Deep and broad, an average of 9 mm in depth and 30 mm in width.

*Stalk.*—Thin to medium thickness, an average of 2.2 mm thick and 34 mm in length.

*Depth of stalk cavity.*—Broad and medium depth, an average of 21 mm in depth, and 36 mm in width.

*Relief of surface.*—Smooth.

*Skin.*—Medium waxinesss, bloom not present, texture; translucent, thin, and smooth.

*Skin color.*—53B.

*Presence of russet.*—Very low to low level on cheeks.

*Lenticels.*—Small to medium (average of 21 mm), slightly prominent.

*Color of flesh.*—158B.

*Distinctness of core line.*—Medium.

*Aperture of locules.*—Moderately open.

*Fruit set.*—Intermediate to good.

*Fruit maturity date.*—Mid to late, average harvest date is October 8$^{th}$ in Summerland, BC, Canada.

*Browning of flesh.*—Medium to strong.

*Firmness* (*without skin*).—Firm to very firm.

*Texture of flesh.*—Intermediate.

*Cropping frequency.*—Annual to sometimes biennial.

*Fruit flavor.*—Sweet-tart.

*Acidity.*—An average of 0.57 titratable acidity (malic acid equivalent).

*Brix.*—An average of 14.

*Seed.*—199C in color when dry, ovoid to somewhat deltoid in shape, an average of 8.9 mm in length and 5.0 mm in width and 2.65 mm in thickness.

*Storage life.*—6 months in common storage (average temperature of 34° F.), unusually long storage life.

It is claimed:

1. A new and distinct variety of apple tree named 'SPA493' as herein illustrated and described.

* * * * *